(12) United States Patent
Khenansho

(10) Patent No.: US 10,610,390 B2
(45) Date of Patent: *Apr. 7, 2020

(54) IMPLANT DELIVERY SYSTEM AND METHOD OF USE

(71) Applicants: STRYKER CORPORATION, Kalamazoo, MI (US); STRYKER EUROPEAN HOLDINGS I, LLC, Kalamazoo, MI (US)

(72) Inventor: Michael Khenansho, San Jose, CA (US)

(73) Assignee: Stryker, Inc., Kalamazoo, MI (US)

(*) Notice: Subject to any disclaimer, the term of this patent is extended or adjusted under 35 U.S.C. 154(b) by 165 days.

This patent is subject to a terminal disclaimer.

(21) Appl. No.: 15/708,028

(22) Filed: Sep. 18, 2017

(65) Prior Publication Data

US 2018/0008440 A1 Jan. 11, 2018

Related U.S. Application Data

(63) Continuation of application No. 15/129,592, filed as application No. PCT/US2015/024535 on Apr. 6, 2015, now Pat. No. 9,775,732.

(Continued)

(51) Int. Cl.
*A61F 2/95* (2013.01)
*A61F 2/966* (2013.01)
(Continued)

(52) U.S. Cl.
CPC .............. *A61F 2/95* (2013.01); *A61F 2/958* (2013.01); *A61F 2/966* (2013.01); *A61M 25/10* (2013.01);
(Continued)

(58) Field of Classification Search
CPC .......... A61M 25/10; A61M 2025/1056; A61F 2230/0093; A61F 2250/0003; A61F 2/958;
(Continued)

(56) References Cited

U.S. PATENT DOCUMENTS

| 4,649,922 A | * | 3/1987 | Wiktor | A61F 2/958 606/194 |
| 4,733,665 A | * | 3/1988 | Palmaz | A61F 2/915 606/108 |

(Continued)

FOREIGN PATENT DOCUMENTS

| WO | 2007/109621 | 9/2007 |
| WO | 2008/135260 | 11/2008 |
| WO | 2015/157181 | 10/2015 |

OTHER PUBLICATIONS

PCT International Search Report and Written Opinion for International Appln. No. PCT/US2015/024535, Applicant Stryker Corporation, forms PCT/ISA/210, 220, and 237, dated Jun. 24, 2015 (14 pages).

*Primary Examiner* — Phong Son H Dang
(74) *Attorney, Agent, or Firm* — Vista IP Law Group, LLP

(57) ABSTRACT

An implant delivery system including a catheter having a delivery lumen; a pusher member slidably disposed in the catheter delivery lumen; a retaining member coupled to a distal end portion of the pusher member, the retaining member configured to retain an expandable implant in a collapsed configuration on the pusher member for delivery of the implant through the catheter delivery lumen; and an expandable actuator coupled to the distal end portion of the pusher member and operatively associated with the retaining member, wherein expansion of the actuator causes the retaining member to disengage from an implant carried on (Continued)

the pusher member, to thereby allow the implant to expand from the collapsed configuration.

9 Claims, 7 Drawing Sheets

Related U.S. Application Data

(60) Provisional application No. 61/976,653, filed on Apr. 8, 2014.

(51) Int. Cl.
 *A61F 2/958* (2013.01)
 *A61M 25/10* (2013.01)

(52) U.S. Cl.
 CPC ........... A61F 2002/9583 (2013.01); *A61F 2230/0093* (2013.01); *A61F 2250/0003* (2013.01); *A61M 2025/1056* (2013.01)

(58) Field of Classification Search
 CPC .. A61F 2/9583; A61F 2002/9583; A61F 2/95; A61F 2/962; A61F 2/966; A61F 2/9665
 See application file for complete search history.

(56) References Cited

U.S. PATENT DOCUMENTS

| | | | | |
|---|---|---|---|---|
| 4,762,128 A * | 8/1988 | Rosenbluth | | A61F 2/04 604/103.08 |
| 4,955,895 A * | 9/1990 | Sugiyama | | A61M 25/104 604/103.1 |
| 5,085,636 A * | 2/1992 | Burns | | A61M 25/0075 604/913 |
| 5,151,105 A | 9/1992 | Kwan-Gett | | |
| 5,545,209 A * | 8/1996 | Roberts | | A61F 2/958 604/103.05 |
| 5,695,468 A * | 12/1997 | Lafontaine | | A61M 25/1018 604/96.01 |
| 5,702,419 A * | 12/1997 | Berry | | A61F 2/91 606/108 |
| 5,810,871 A * | 9/1998 | Tuckey | | A61F 2/958 606/108 |
| 5,910,144 A * | 6/1999 | Hayashi | | A61B 17/221 606/108 |
| 5,980,530 A * | 11/1999 | Willard | | A61F 2/958 606/195 |
| 6,051,001 A * | 4/2000 | Borghi | | A61F 2/958 606/198 |
| 6,264,683 B1 * | 7/2001 | Stack | | A61F 2/958 623/1.11 |
| 6,380,457 B1 * | 4/2002 | Yurek | | A61F 2/95 623/1.11 |
| 6,547,762 B1 * | 4/2003 | Botich | | A61M 25/0631 604/110 |
| 6,726,714 B2 * | 4/2004 | DiCaprio | | A61F 2/958 623/1.11 |
| 6,830,575 B2 * | 12/2004 | Stenzel | | A61F 2/95 606/108 |
| 6,872,223 B2 * | 3/2005 | Roberts | | A61F 2/958 623/1.11 |
| 7,169,172 B2 * | 1/2007 | Levine | | A61F 2/95 623/1.11 |
| 7,547,311 B2 * | 6/2009 | Ortiz | | A61B 17/08 606/142 |
| 7,632,296 B2 * | 12/2009 | Malewicz | | A61F 2/966 623/1.11 |
| 7,794,487 B2 * | 9/2010 | Majercak | | A61F 2/95 623/1.11 |
| 7,993,392 B2 * | 8/2011 | Righini | | A61F 2/2436 623/2.11 |
| 8,157,852 B2 * | 4/2012 | Bloom | | A61F 2/2412 623/1.11 |
| 8,236,042 B2 * | 8/2012 | Berez | | A61B 17/12022 623/1.12 |
| 8,267,985 B2 * | 9/2012 | Garcia | | A61B 17/12022 623/1.11 |
| 8,313,525 B2 * | 11/2012 | Tuval | | A61F 2/2418 623/2.11 |
| 8,986,362 B2 * | 3/2015 | Snow | | A61F 2/95 606/108 |
| 9,119,716 B2 * | 9/2015 | Lee | | A61F 2/958 |
| 9,277,993 B2 * | 3/2016 | Gamarra | | A61F 2/2436 |
| 2001/0027337 A1 * | 10/2001 | Di Caprio | | A61F 2/958 623/1.11 |
| 2004/0236406 A1 | 11/2004 | Gregorich | | |
| 2006/0025844 A1 * | 2/2006 | Majercak | | A61F 2/95 623/1.11 |
| 2008/0114442 A1 * | 5/2008 | Mitchell | | A61F 2/07 623/1.13 |
| 2008/0119922 A1 * | 5/2008 | Alkhatib | | A61F 2/958 623/1.11 |
| 2008/0132989 A1 * | 6/2008 | Snow | | A61F 2/95 623/1.12 |
| 2008/0255506 A1 * | 10/2008 | Wilson | | A61B 17/11 604/97.01 |
| 2009/0069889 A1 * | 3/2009 | Suri | | A61F 2/2433 623/2.11 |
| 2009/0287292 A1 * | 11/2009 | Becking | | A61F 2/95 623/1.11 |
| 2010/0100167 A1 * | 4/2010 | Bortlein | | A61F 2/2436 623/1.11 |
| 2011/0112623 A1 * | 5/2011 | Schatz | | A61F 2/958 623/1.11 |
| 2011/0208292 A1 * | 8/2011 | Von Oepen | | A61F 2/97 623/1.23 |
| 2012/0143129 A1 * | 6/2012 | Simpson | | A61M 25/1036 604/96.01 |
| 2012/0148175 A1 * | 6/2012 | Wesselmann | | A61M 25/01 384/15 |
| 2013/0218266 A1 * | 8/2013 | Chalekian | | A61F 2/2433 623/2.11 |
| 2013/0226278 A1 * | 8/2013 | Newell | | A61F 2/966 623/1.12 |
| 2013/0345628 A1 * | 12/2013 | Berger | | A61M 25/003 604/101.05 |
| 2014/0200648 A1 * | 7/2014 | Newell | | A61F 2/844 623/1.11 |
| 2014/0276530 A1 * | 9/2014 | Gianotti | | A61M 25/1002 604/500 |
| 2015/0209019 A1 * | 7/2015 | Yassinzadeh | | A61B 17/0057 606/213 |

\* cited by examiner

IMPLANT DELIVERY SYSTEM AND METHOD OF USE

CROSS-REFERENCE TO RELATED APPLICATIONS

The present application is a continuation of pending U.S. patent application Ser. No. 15/129,592, filed Sep. 27, 2016, which is a National Phase entry under 35 U.S.C. § 371 of International Patent Application No. PCT/US15/24535, having an international filing date of Apr. 6, 2015, which claims the benefit under 35 U.S.C. § 119 to U.S. Provisional Application Ser. No. 61/976,653, filed Apr. 8, 2014. The foregoing applications are hereby incorporated by reference into the present application in their entirety.

FIELD OF INVENTION

The disclosed inventions pertain generally to systems and methods for delivering medical implants. More particularly, the disclosed inventions pertain to delivery systems and methods for delivering tubular prosthesis to a target site in a vasculature of a patient.

BACKGROUND

The use of intravascular medical devices and implants has become an effective method for treating many types of vascular disease. In general, a suitable intravascular device is inserted into the vascular system of the patient and navigated through the vasculature to a target site in a patient. Using this method, virtually any target site in the patient's vascular system may be accessed, including the coronary, cerebral, and peripheral vasculature.

Catheters are often utilized to place medical implants, such as stents and embolic devices, at a desired location within a body. Usually, stents are tubular prosthesis for insertion through body lumens; although, stents may have a wide variety of sizes and shapes. A stent may be delivered by being mounted over a balloon and loaded onto a catheter, and after positioning the stent at the desired location, the balloon is inflated to expand the stent radially outward. Alternatively, a stent may be loaded onto a catheter in a reduced configuration and/or diameter; then introduced into the lumen of a body vessel. For example, self-expanding stents are to be delivered in an elastically compressed or collapsed state while being confined within a tubular restraining member, such as a catheter. The catheter is threaded through the vascular system until its distal end reaches the implantation site. Additionally, the catheter may be introduced into the patient over a guidewire which has been previously introduced, in the so-called "over-the-wire" and "rapid-exchanged" delivery systems. The collapsed stent is mounted on or distally located from a pusher member disposed within the catheter, so that the stent is introduced, advanced or pushed through the catheter. When the stent is positioned adjacent to the desired location, it is pushed out of the catheter (i.e., unsheathed; which may include withdrawal of the catheter) and allowed to expand to a predetermined diameter in the body vessel, engaging the interior walls of the vessel, without requiring assistance from a balloon.

A self-expanding stent may be biased so as to expand upon release from the delivery catheter and/or includes a shape-memory component which allows the stent to expand upon exposure to a predetermined condition. Some stents may be characterized as hybrid stents which have some characteristics of both self-expandable and balloon expandable stents. In either stent configuration, once delivered to a target location within the body, the expanded or enlarged stent supports and reinforces the vessel wall while maintaining the vessel in an open and unobstructed condition.

Some stent delivery systems have the inability to protect the distal end of a self-expanding stent when the stent is pushed through a catheter. Other delivery systems include a retaining member that engages the distal end of the stent mounted on a pusher member. With some frequency, when the self-expanding stent is unsheathed and/or pushed out of the catheter in delivery systems having a retaining member, the distal end of the stent is undesirably held by the retaining member, so the stent is not allowed to expand and be deployed at the target location. Thus, there may be an increased risk of failure and duration of the medical procedure, or at least, a failure to deliver the stent in a target location, when the stent distal end is undesirably held by the retaining member after the stent is pushed out of the catheter or the catheter is unsheathed. Accordingly, there is an ongoing need to provide an implant delivery system for delivering self-expanding stents that preserves the integrity the distal end of the stent when pushed through a catheter for deployment, and provides a controlled delivery and release of the distal end of a self-expanding stent during deployment into a target location.

SUMMARY

In one embodiment of the disclosed inventions, a medical assembly for delivering an implant into a target site of a patient includes a catheter having a delivery lumen; a pusher member slidably disposed in the catheter delivery lumen; a retaining member coupled to a distal end portion of the pusher member, the retaining member configured to retain an expandable implant in a collapsed configuration on the pusher member for delivery of the implant through the catheter delivery lumen; and an expandable actuator coupled to the distal end portion of the pusher member and operatively associated with the retaining member, wherein expansion of the actuator causes the retaining member to disengage from an implant carried on the pusher member, to thereby allow the implant to expand from the collapsed configuration. By way of non-limiting example, the actuator may be an inflatable membrane, and the pusher member comprising an inflation lumen in communication with an interior region defined by the membrane, wherein the retaining member may be affixed to the membrane.

In various embodiments, the system further includes an expandable implant carried on the pusher member, the retaining member comprising a first end attached to the pusher member at a location distal to the implant, and a second end releasably engaging the implant to thereby retain the implant in the collapsed configuration on the pusher member. The retaining member may be biased to retain the implant in the collapsed configuration on the pusher member. The expandable implant may be a tubular stent or blood flow diverter.

In various embodiments, the pusher member comprises a stop member proximally disposed to the expandable implant carried on the pusher member, wherein the stop member limits translation movement of the implant in its collapsed configuration. The stop member may be, for example, an annular ring or a plurality of protrusions disposed on the pusher member.

In various embodiments, the system may further comprise a guidewire disposed within the inflation lumen of the pusher member, with a seal member disposed distally to the expandable actuator of the pusher member, the seal member having an opening to allow passage of the guidewire.

In one embodiment, an implant delivery system includes a catheter having a delivery lumen, with a pusher member slidably disposed in the catheter delivery lumen; an expandable implant carried on a distal end portion of the pusher member; a plurality of retention members, each having a first end attached to the pusher member at a location distal to the implant, and a second end releasably engaging the implant to thereby retain the implant in the collapsed configuration on the pusher member for delivery of the implant through the catheter delivery lumen; and an inflatable membrane attached to the pusher member and having an exterior surface affixed to the respective retention members, the pusher member comprising an inflation lumen in communication with an interior region defined by the membrane, wherein inflation of the membrane causes the retaining members to disengage the implant and thereby allow the implant to expand from the collapsed configuration. By way of non-limiting example, the respective first ends of the retention members may be pivotally attached to the pusher member, wherein the retention members are biased to retain the implant in the collapsed configuration on the pusher member.

In accordance with another embodiment of the disclosed inventions, a method of delivering an implant to a target site in a body lumen is provided, wherein the implant has a collapsed delivery configuration, and an expanded implanted configuration, the method including the acts of inserting a catheter into the body lumen, until an open distal end of the catheter is proximate the target site in the body lumen; advancing a pusher member having the implant loaded thereon in the collapsed configuration through a delivery lumen of the catheter, until the implant is positioned adjacent the open distal end of the catheter, wherein the implant is releasably retained in the collapsed configuration on the pusher member by a retaining member coupled to the pusher member distal to the implant; advancing the implant out the open distal end of the catheter and into the body lumen proximate the target site by one or both of withdrawing the catheter relative to the pusher member, or further advancing the pusher member relative to the catheter; and expanding an actuator coupled to the distal end portion of the pusher member, wherein expansion of the actuator causes the retaining member to disengage the implant and thereby allow the implant to expand from the collapsed configuration to the expanded configuration.

In accordance with this embodiment, the actuator may be an inflatable membrane, and the pusher member comprising a lumen in communication with an interior region defined by the membrane, wherein expanding the actuator comprises supplying an inflation medium through the pusher member lumen to inflate the membrane. The membrane may be affixed to the retaining member, and after inflating the membrane to disengage the retaining member from the implant and thereby allow the implant to expand from the collapsed configuration to the expanded configuration, the method further includes supplying a vacuum through the pusher member lumen to deflate the membrane, and thereby collapse the retaining member towards the pusher member, and withdrawing the pusher member and retaining member into the catheter. Optionally, the retention member may be biased to retain the implant in the collapsed configuration on the pusher member.

Other and further aspects and features of embodiments of the disclosed inventions will become apparent from the ensuing detailed description in view of the accompanying figures.

DETAILED DESCRIPTION

Figure 1A:
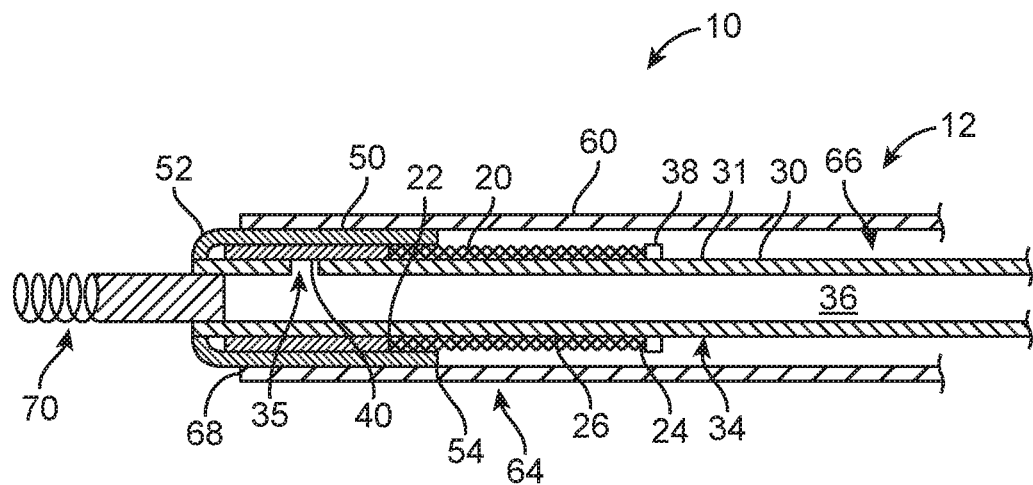
FIGS. 1A-B are cross-sectional views of an implant delivery system constructed according to one embodiment of the disclosed inventions.

For the following defined terms, these definitions shall apply, unless a different definition is set forth in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 1B:
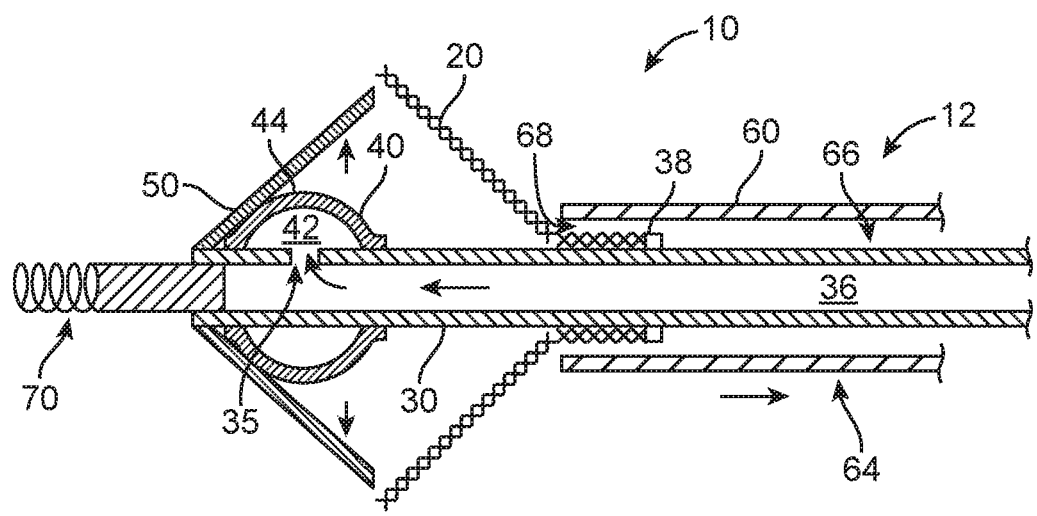
Figure 6A:
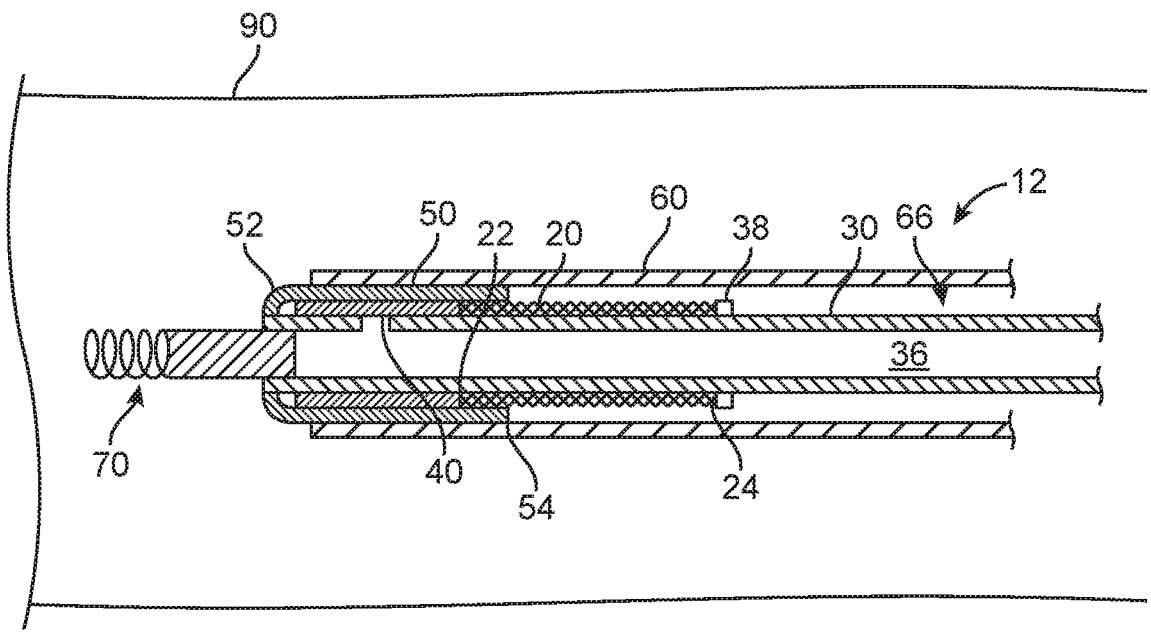
FIGS. 6A-G are cross-sectional views of a method of delivering an implant into a target site of a patient using the implant delivery system of FIGS. 1A-B.

FIGS. 1A-B are cross-sectional views of a medical assembly 10 for delivering an expandable implant 20 into a target site of a patient, constructed in accordance with a one embodiment of the disclosed inventions. The medical assembly 10 includes an implant 20, such a stent, and a delivery system 12 to which the implant 20 is detachably coupled. The delivery system 12 and implant 20 may be composed of suitable polymeric materials, metals and/or alloys, such as polyethylene, stainless steel or other suitable biocompatible materials or combinations thereof. The delivery system 12 is dimensioned to reach remote locations of a vasculature and is configured to deliver the implant 20 to a target location in a patient's body, such as an occlusion in a blood vessel. The delivery system 12 includes a delivery configuration in which a retaining member 50 is collapsed retaining the implant 20 in a radially constrained and collapsed configuration (FIGS. 1A, 6A). The delivery system further includes a deployed configuration in which the retaining member 50 is outwardly expanded allowing the implant 20 to expand into a deployed configuration and be deployed out of the delivery system 12 (FIGS. 1B, 6C).

The implant 20 includes a tubular resilient member having a proximal end 22, a distal end 24, and defining an inner lumen 26 extending therebetween. The implant 20 is biased to extend radially outwards upon release from the delivery system 12. The implant 20 comprises a collapsed configuration (FIGS. 1A, 2A-B, 6A-B), and an expanded configuration (FIGS. 1B, 6C-F). The implant 20 may be constructed from a variety of materials such as stainless steel, elgiloy, nickel, titanium, nitinol, shape memory polymers, or combinations thereof. The implant 20 may also be formed in a variety of manners as well. For example, the implant 20 may be formed by etching or cutting a pattern from a tube or sheet of stent material; a sheet of stent material may be cut or etched according to a desired stent pattern whereupon the sheet may be rolled or otherwise formed into the desired substantially tubular, bifurcated or other shape. For the implant 20, one or more wires or ribbons of stent material may be woven, braided or otherwise formed into a desired shape and pattern. The implant 20 may include further components that are welded, bonded or otherwise engaged to one another.

The delivery system 12 includes a tubular member interface having a catheter 60 (i.e. outer tubular member), and a pusher member 30 (i.e. inner tubular member). The pusher member 30 is coaxially disposed within the catheter 60 and movable relative (i.e. translation and rotation) to the catheter 60. The catheter 60 has a proximal end portion (not shown), a distal end portion 64 including open distal end 68, and defining a delivery lumen 66 extending between the proximal end portion and the distal end portion 64. The pusher member 30 has a proximal end portion (not shown), a distal end portion 34, and an inflation lumen 36 extending therebetween. The distal end portion 34 of the pusher member 30 includes an expandable actuator 40 in fluid communication with the inflation lumen 36 for inflation and deflation. The distal end portion 34 further includes an inflation opening 35 that allows for fluid communication between the inflation lumen 36 and the expandable actuator 40, and a non-traumatic distal tip 70 creating a tight-fluid seal distally located to the inflation opening 35.

An inflation source and/or vacuum (not shown) is fluidly coupled to the inflation lumen 36 to deliver and withdraw fluid and/or gas to and from an interior region 42 defined by the expandable actuator 40 via the inflation opening 35. The inflation opening 35 may comprise a plurality of openings (not shown) in fluid communication with the interior region 42 of the expandable actuator 40. The expandable actuator 40 that is coupled to the distal end portion 34 of the pusher member 30, comprises an expandable membrane, a balloon or the like, or combinations thereof. The expandable actuator 40 may be made of, or otherwise include polymeric materials, such as silicone, urethane polymer, thermoplastic elastomers rubber, such as santoprene, nylon, and polyethylene terephthalate (PET) and other suitable materials or combinations thereof.

The distal end portion 34 of the pusher member 30 further includes a retaining member 50. The retaining member 50 has a first end 52 fixedly attached to the pusher member 30 and a second end 54 releasably engaging the implant 20. The first end 52 is attached to the pusher member 30 by an adhesive, thermal bonding or the like, mechanical fastening, sutures or combinations thereof. The second end 54 retains the implant 20 in the collapsed configuration on the pusher member 30 for delivery of the implant 20 through the catheter delivery lumen 66. The retaining member 50 is disposed over the expandable actuator 40 and is affixed to at least a portion or an exterior surface 44 of the expandable actuator 40, so that when the expandable actuator 40 expands, the actuator 40 causes the retaining member 50 to disengage from the implant 20 carried on the pusher member 30 allowing the implant 20 to expand from the collapsed configuration (FIG. 1B).

Figure 3A:
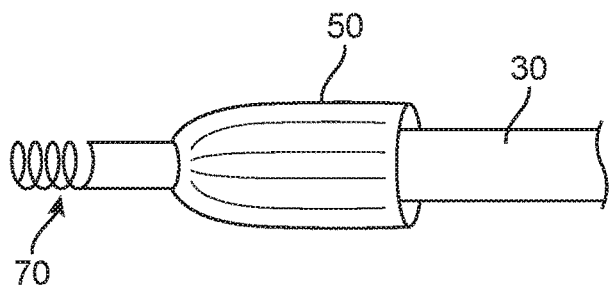
FIGS. 3A-B are perspective views of a retaining member according to an embodiment of the disclosed inventions.
Figure 3B:
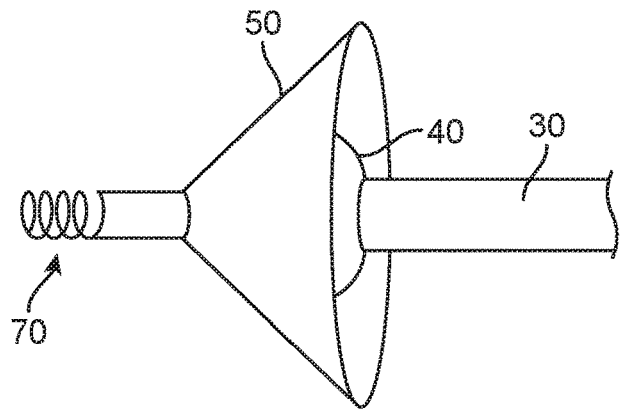

The retaining member 50 is affixed to the expandable actuator 40 with the use of adhesive, thermal bonding or the like, mechanical fastening, sutures or combinations thereof. The retaining member 50 may comprise a shape memory material, like nitinol, and may be biased to retain the implant 20 in the collapsed configuration. The retaining member 50 may include a funnel-like, shirk-like, conical configuration or the like (FIGS. 3A-B) that is configured to flare open and extend radially outwards when the expandable actuator 40 is inflated and expands (FIG. 3B).

Figure 4A:
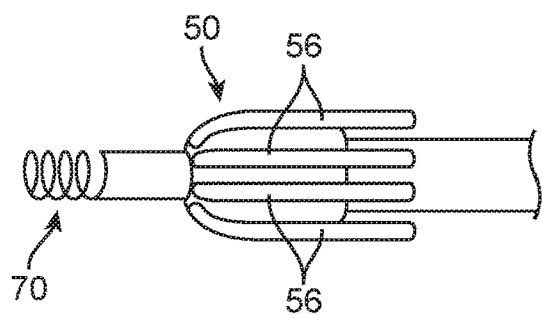
FIGS. 4A-B are perspective views of a plurality of retaining members according to another embodiment of the disclosed inventions.
Figure 4B:
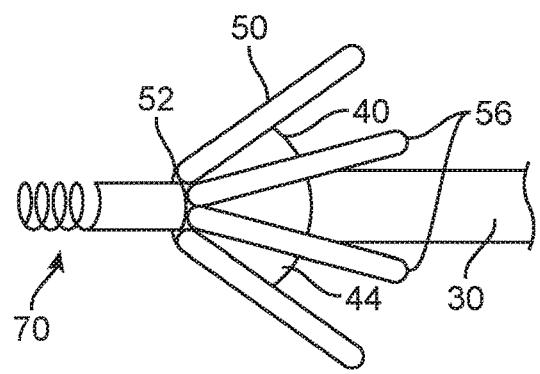

In an alternative embodiment, the retaining member 50 comprises a plurality of retention members 56 (FIGS. 4A-B). The plurality of retention members 56 are secured to the pusher member 30 at their respective first ends 52, and are releasably engaged to the implant 20 at their respective second ends 54. The respective first ends 52 of the plurality of retention members 56 are pivotally attached to the pusher member 30. The plurality of retention members 56 are disposed over and affixed to at least a portion of the expandable actuator 40 or the exterior surface 44 of the expandable actuator 40. The plurality of retention members 56 may be biased to retain the implant 20 in the collapsed configuration. The plurality of retention members 56 are configured to pivot at their first ends 52 and extend radially outwards at their second ends 54 when the expandable actuator 40 is inflated and expands (FIG. 4B).

Figure 5A:
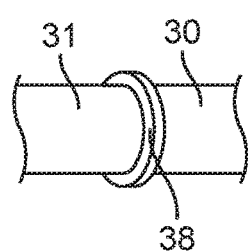
FIGS. 5A-B are perspective views of a stop members according to embodiments of the disclosed inventions.
Figure 5B:
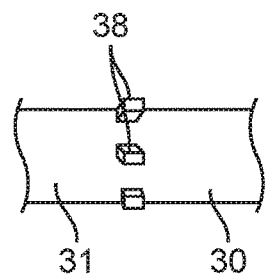

Referring back to FIG. 1A, in the delivery configuration of the system 12, the implant 20 is mounted and disposed on the pusher member 30, proximally located to the expandable actuator 40. The second end 54 of the retaining member 50 extends over the distal end 24 of the implant 20, so that the retaining member 50 retains the implant 20 in the collapsed configuration on the pusher member 30 for delivery of the implant 20 through the catheter delivery lumen 66. Further, the distal end portion 34 of the pusher member 30 comprises a stop 38 disposed around an outer surface 31 of the pusher member 30 and proximally located to the expandable actuator 40 and the retaining member 50. The stop 38 limits the movement (i.e. translation) of the implant 20 in a proximal direction, when the system 12 is in the delivery configuration. The stop may include a ring configuration (FIG. 5A) or a plurality of protrusions (FIG. 5B) disposed around the outer surface 31 of the pusher member.

Figure 2A:
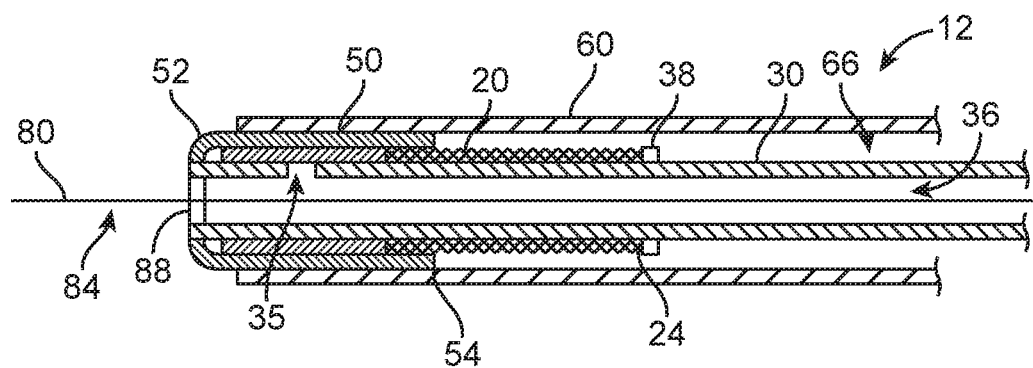
FIGS. 2A-B are cross-sectional views of an implant delivery system constructed according to another embodiment of the disclosed inventions.
Figure 2B:
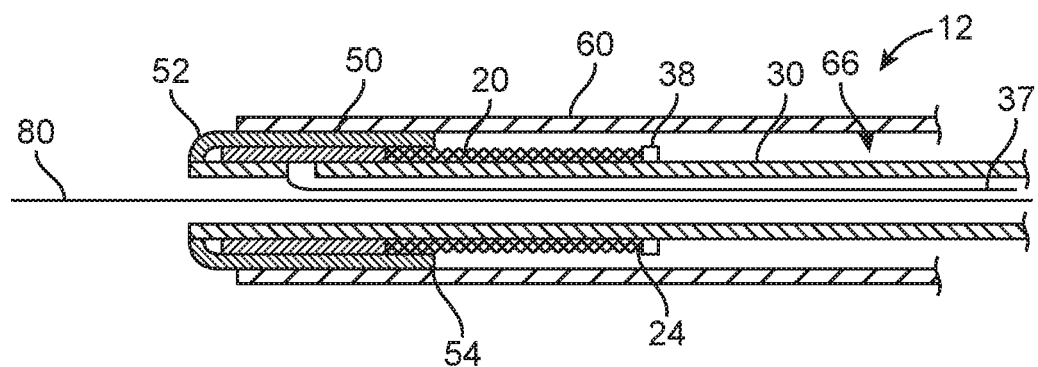

FIGS. 2A-B illustrate the delivery system 12 according to the other embodiments of the disclosed inventions. These delivery systems 12 include a guidewire 80 having a proximal portion (not shown) and a distal portion 84. Generally, the proximal portion may be formed from material that is stiffer than the distal portion 84 of the guidewire 80, so that the proximal portion has sufficient pushability to advance the guidewire 80 through the patient's vascular system, while the distal portion 84 may be formed of a more flexible material that remains flexible and tracks more easily to access remote locations in tortuous regions of the vasculature. In some instances, the proximal portion of the guidewire 80 may include a reinforcement layer, such a braided layer or coiled layer to enhance the pushability of the guidewire 80.

When using the delivery systems 12 of FIGS. 2A-B, the catheter 60 and the pusher member 30 are introduced into the patient over the guidewire 80, which has been previously introduced. The guidewire 80 may extend through the entire length of the catheter 60 and pusher member 30 through the lumen 36. Alternatively, the guidewire 80 may extend through only a distal portion of the catheter 60 and pusher member 30, in the so called "rapid-exchanged" delivery systems (not shown).

The delivery system 12 of FIG. 2A includes a seal member 88 at the distal end portion 34 of the pusher member 30, distally located from the inflation opening 35 of the pusher member 30. The seal member 88 includes an annular configuration to allow passage of the guidewire 80 while creating a fluid-tight seal in the inflation lumen 36 of the pusher member 30 so that the expandable actuator 40 is inflated and deflated. Alternatively, the delivery system 12 of FIG. 2B includes an inflation tubular member 37 disposed within the pusher member 30 and coupled to the inflation opening 35 for inflation and deflation of the expandable actuator 40. The inflation tubular member 37 is fluidly coupled to an inflation source and/or vacuum (not shown) to deliver and withdraw fluid and/or gas to and from the expandable actuator 40.

Figure 6B:
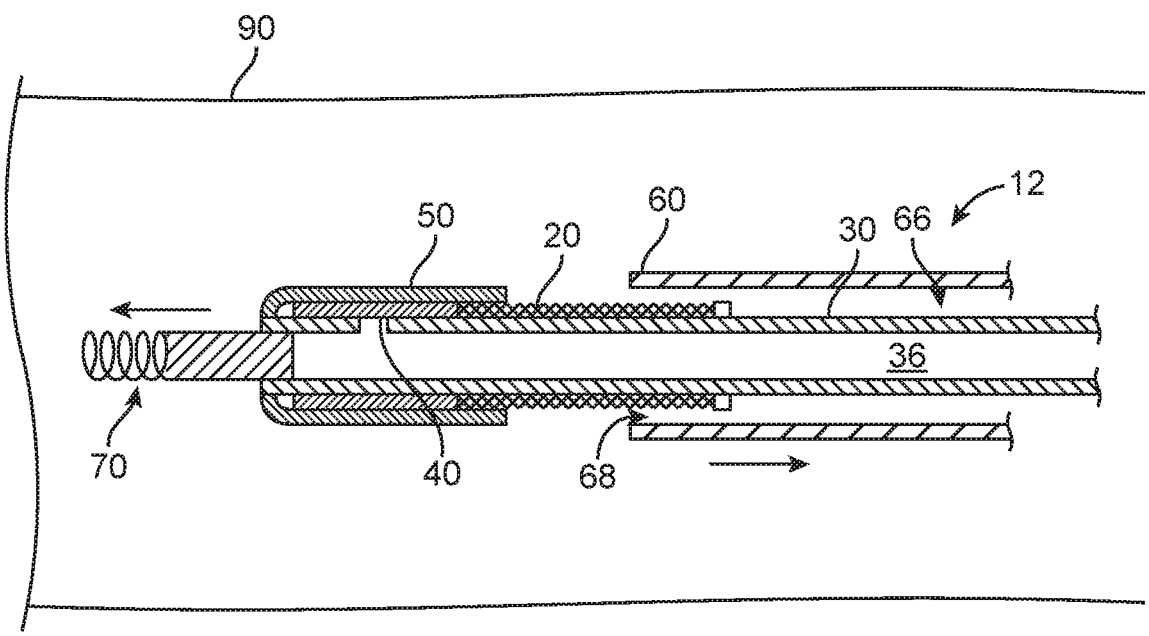
Figure 6C:
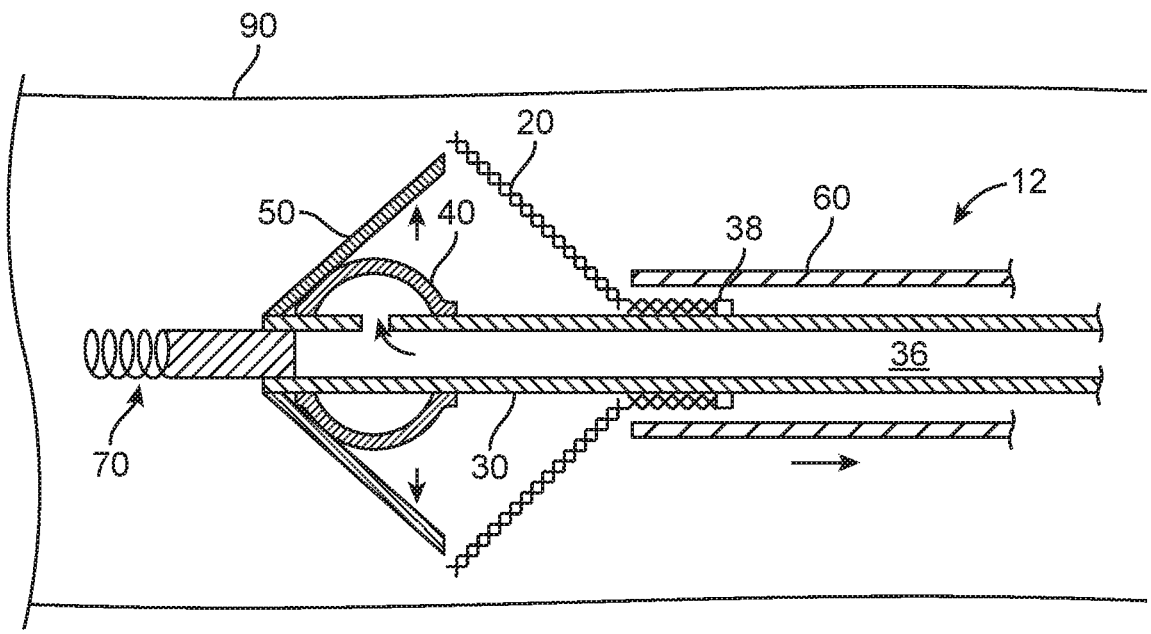
Figure 6D:
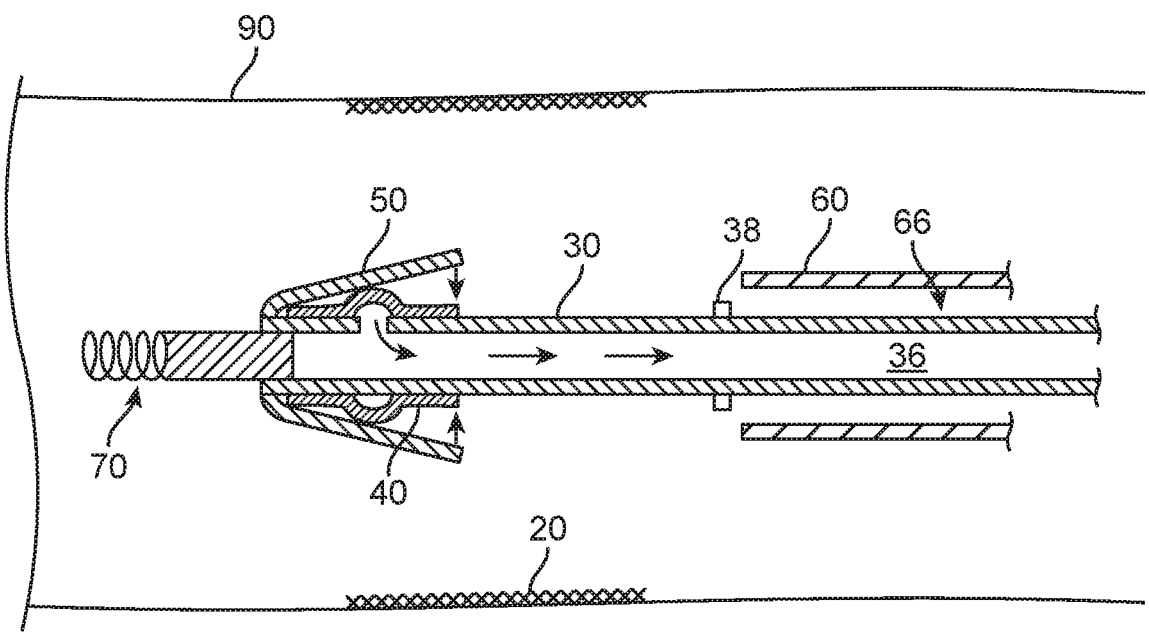
Figure 6E:
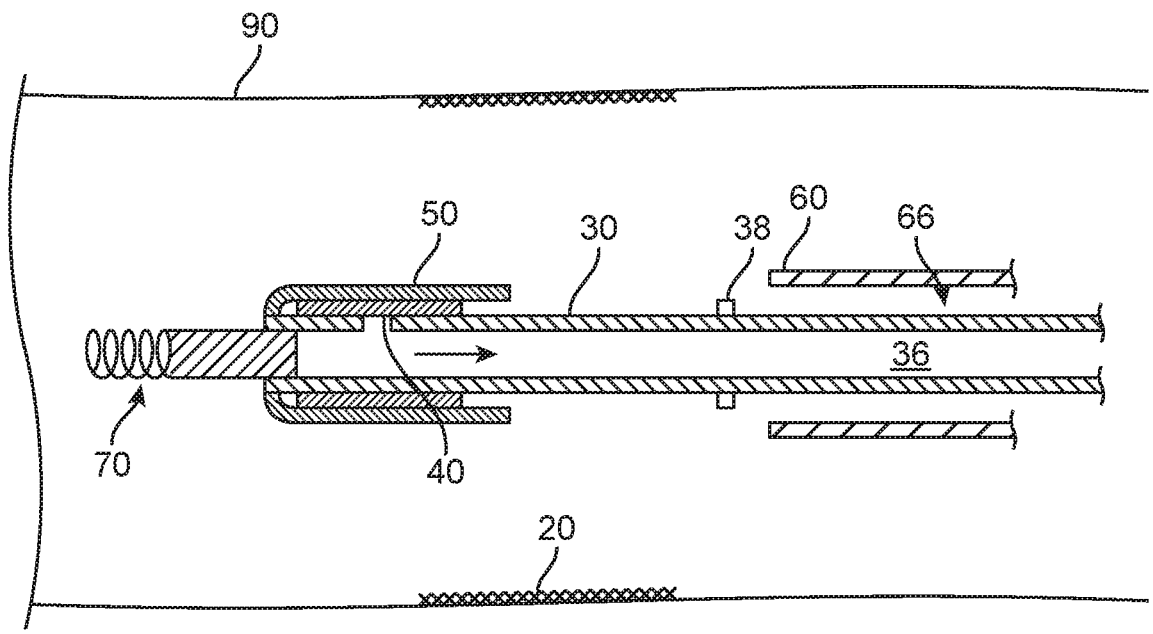

FIGS. 6A-G illustrate an exemplary method of delivering the implant 20 to a target site in a body lumen 90 using the delivery system 12 of FIGS. 1A-B. After gaining access to the vasculature region of a patient, the catheter 60 is inserted into the body lumen 90 and advanced, until the open distal end 68 of the catheter 60 is disposed proximately to the target site in the body lumen 90. Once the open distal end 68 of the catheter 60 has been advanced to the target site, the pusher member 30, having the loaded implant, 20 is advanced through the delivery lumen 66 until the implant 20 is positioned adjacent to the open distal end 68 of the catheter 60 (FIG. 6A). The implant 20 is releasably disposed on the pusher member 30 in the collapsed configuration by the retaining member 50 coupled to the pusher member 30. The implant 20 is then advanced out the open distal end 68 of the catheter 60 and into the body lumen 90 proximate the target site by one or both of, withdrawing the catheter 60 relative to the pusher member 30, or further advancing the pusher member 30 relative to the catheter 60 (FIG. 6B).

The expandable actuator 40 coupled to the distal end portion 34 of the pusher member 30 is then expanded to cause the retaining member 50 to disengage the implant 20 and allow the implant 20 to expand from the collapsed configuration to the expanded configuration (FIG. 6C). The expandable actuator 40 may be expanded concurrently, simultaneously or sequentially to advancing the implant 20 out of the open distal end 68 of the catheter 60. It will be appreciated that the movement of the pusher member 30 relative to the catheter 60 or vice versa, and the expansion of the actuator 40 and the disengagement of the retaining member 50, provides a controlled release of the implant 20, particularly at the distal end 24 of the implant 20.

Figure 6F:
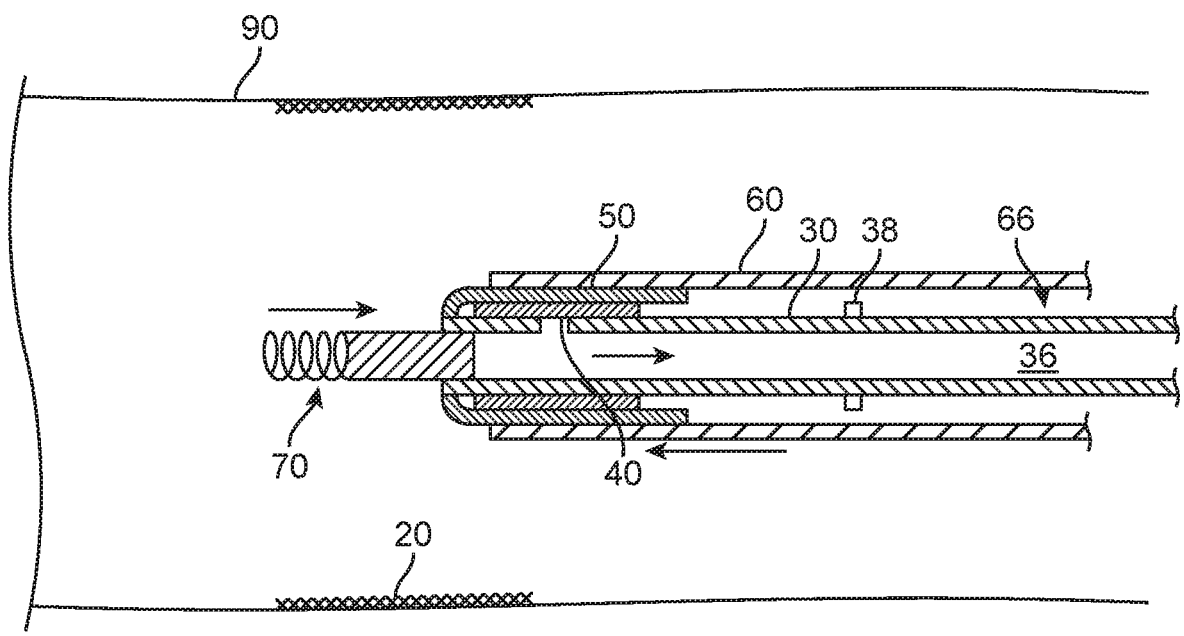
Figure 6G:
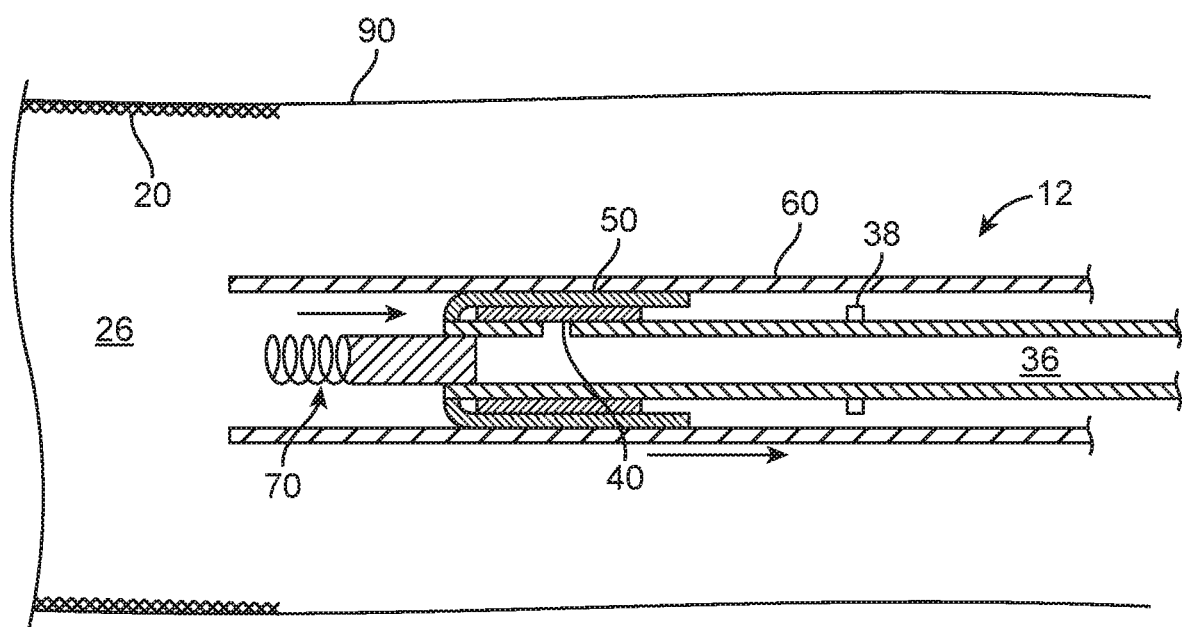

According to the methods of delivering the implant 20, the expandable actuator 40 may include an inflatable membrane 40 having an interior region 42 in fluid communication with the inflation lumen 36 of the pusher member 30, so that the expansion of the actuator 40 comprises supplying an inflation medium (i.e. fluid and/or gas) through the inflation lumen 36 of pusher member 30, to inflate the membrane. Further, according to the method of delivering the implant 20, the expandable actuator 40 (i.e. membrane) is affixed to the retaining member 50, so that after inflating the membrane 40 to disengage the retaining member 50 from the implant 20 and allow the implant 20 to expand from the collapsed configuration to the expanded configuration (FIGS. 6A-C), a vacuum is supplied through the inflation lumen 36 of pusher member 30 to deflate the membrane 40 (FIG. 6D), and thereby collapse the retaining member 50 towards the pusher member 30 (FIG. 6E), and withdrawing the pusher member 30 and retaining member 50 into the catheter 60 (FIG. 6F). After the implant 20 is delivered at the target site (FIGS. 6D-F), the delivery system 12 is withdrawn from the body lumen 90 of the patient (FIG. 6G). In this method, the retention member 50 is biased to retain the implant 20 in the collapsed configuration on the pusher member 30.

It will be appreciated that the exemplary method illustrated in FIGS. 6A-G may also be practiced using the delivery systems 12 of FIGS. 2A-B. Those skilled in the art will appreciate that the delivery systems 12 and methods described herein may be contemplated to deliver tubular prosthesis, implants, stents, fluid diverters or the like for vascular and non-vascular application.

What is claimed is:

1. An implant delivery system, comprising:
   a catheter having a delivery lumen;
   a pusher member slidably disposed in the catheter delivery lumen;
   a retaining member coupled to a distal end portion of the pusher member, the retaining member configured to retain an expandable implant in a collapsed configuration on the pusher member for delivery of the implant through the catheter delivery lumen; and
   an expandable actuator coupled to the distal end portion of the pusher member and operatively associated with the retaining member, wherein expansion of the actuator causes the retaining member to disengage from the implant carried on the pusher member, to thereby allow the implant to expand from the collapsed configuration, wherein the actuator comprises an inflatable membrane, and the pusher member comprises an inflation lumen in communication with an interior region defined by the membrane, and wherein the retaining member is affixed to the membrane.

2. The system of claim 1, further comprising the expandable implant carried on the pusher member, the retaining member comprising a first end attached to the pusher member at a location distal to the implant, and a second end releasably engaging the implant to thereby retain the implant in the collapsed configuration on the pusher member, wherein the retaining member is biased to retain the implant in the collapsed configuration on the pusher member.

3. The system of claim 2, wherein the expandable implant comprises a tubular body.

4. An implant delivery system, comprising:
   a catheter having a delivery lumen;

a pusher member slidably disposed in the catheter delivery lumen;

an expandable implant carried on a distal end portion of the pusher member;

a plurality of retention members, each having a first end attached to the pusher member at a location distal to the implant, and a second end releasably engaging the implant to thereby retain the implant in a collapsed configuration on the pusher member for delivery of the implant through the catheter delivery lumen; and an inflatable membrane attached to the pusher member and having an exterior surface affixed to the respective retention members, the pusher member comprising an inflation lumen in communication with an interior region defined by the membrane, wherein inflation of the membrane causes the retaining members to disengage the implant and thereby allow the implant to expand from the collapsed configuration.

5. The system of claim 4, wherein the respective first ends of the retention members are pivotally attached to the pusher member.

6. The system of claim 4, wherein the retention members are biased to retain the implant in the collapsed configuration on the pusher member.

7. The system of claim 4, wherein the pusher member comprises a stop member proximally disposed to the expandable implant carried on the pusher member, wherein the stop member limits translation movement of the implant in its collapsed configuration.

8. The system of claim 7, wherein the stop member comprises an annular ring or a plurality of protrusions disposed on the pusher member.

9. The system of claim 4, further comprising a guidewire disposed within the inflation lumen of the pusher member, and a seal member disposed distally to the expandable actuator of the pusher member, wherein the seal member has an opening therethrough to allow passage of the guidewire.

* * * * *